(12) United States Patent
Hettrick et al.

(10) Patent No.: US 7,927,282 B2
(45) Date of Patent: Apr. 19, 2011

(54) SYSTEM AND METHOD OF DETERMINING CARDIAC PRESSURE

(75) Inventors: Douglas A. Hettrick, Blaine, MN (US); Todd M. Zielinski, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 896 days.

(21) Appl. No.: 11/184,438

(22) Filed: Jul. 19, 2005

(65) Prior Publication Data

US 2007/0021665 A1    Jan. 25, 2007

(51) Int. Cl.
*A61B 5/04* (2006.01)
*A61B 5/02* (2006.01)
*A61N 1/00* (2006.01)

(52) U.S. Cl. ........ 600/486; 600/375; 600/387; 607/126; 607/128

(58) Field of Classification Search .................. 600/375, 600/378, 486, 561, 587–594; 607/126–131
See application file for complete search history.

(56) References Cited

U.S. PATENT DOCUMENTS

| | | | |
|---|---|---|---|
| 4,967,755 A | 11/1990 | Pohndorf | |
| 5,324,326 A | 6/1994 | Lubin | |
| 5,353,800 A | 10/1994 | Pohndorf et al. | |
| 5,368,040 A | 11/1994 | Carney | |
| 5,843,135 A | 12/1998 | Weijand et al. | |
| 5,902,331 A | 5/1999 | Bonner et al. | |
| 5,919,221 A | 7/1999 | Miesel | |
| 6,042,537 A * | 3/2000 | Kaiser | 600/38 |
| 6,152,885 A | 11/2000 | Taepke | |
| 6,171,252 B1 | 1/2001 | Roberts | |
| 6,221,024 B1 | 4/2001 | Miesel | |
| 6,223,081 B1 | 4/2001 | Kerver | |
| 6,783,499 B2 * | 8/2004 | Schwartz | 600/486 |
| 2002/0077555 A1 * | 6/2002 | Schwartz | 600/486 |
| 2002/0120200 A1 * | 8/2002 | Brockway et al. | 600/488 |
| 2002/0138124 A1 | 9/2002 | Helfer et al. | |
| 2003/0055344 A1 | 3/2003 | Eigler et al. | |
| 2003/0060685 A1 * | 3/2003 | Houser et al. | 600/206 |
| 2003/0199962 A1 * | 10/2003 | Struble et al. | 607/126 |
| 2004/0147969 A1 * | 7/2004 | Mann et al. | 607/17 |
| 2005/0288596 A1 * | 12/2005 | Eigler et al. | 600/485 |
| 2005/0288722 A1 * | 12/2005 | Eigler et al. | 607/9 |

FOREIGN PATENT DOCUMENTS

WO    WO02065894 A2    8/2002

\* cited by examiner

*Primary Examiner* — Patricia C Mallari
*Assistant Examiner* — Christian Jang
(74) *Attorney, Agent, or Firm* — Michael C. Soldner

(57) ABSTRACT

A pressure sensor is deployed in the right atrium and is in contact with the tissue of the fossa ovalis. The fossa ovalis acts as a membrane and the pressure sensor determines the relative and/or absolute pressure within the left atrium while remaining within the right atrium. A variety of embodiment are provided to deploy and anchor the sensor into the proper position.

26 Claims, 18 Drawing Sheets

SYSTEM AND METHOD OF DETERMINING CARDIAC PRESSURE

FIELD OF THE INVENTION

The present invention relates to implantable medical devices. More specifically, the present invention relates to implantable medical devices that sense or measure pressure.

DESCRIPTION OF THE RELATED ART

There are a number of implantable medical devices (IMDs) that sense various physiological parameters and/or provide a variety of therapies. For example, implantable pulse generators (IPG) typically include one or more leads that are in contact with cardiac tissue to sense electrical depolarization and provide pacing stimuli. Implantable cardioverter/defibrillators (ICD) also typically include one or more leads and provide a larger stimulus for cardioversion or to defibrillate the heart. Often, IMDs include both pacing and cardioversion/defibrillation capabilities.

A housing containing the pulse generator, battery, capacitors, processor, memory, circuitry, etc. is implanted subcutaneously. One or more leads are delivered transvenously such that electrodes forming a portion of the lead are disposed within or contacting an outer portion of the heart. The housing, or "can", may also include one or more electrodes that are selectively used in combination with the various lead electrodes.

In general, the leads sense electrical activity of the heart, typically represented as an electrogram (EGM), which is indicative of the cardiac depolarization waveform and indicates the timing of the various components of the complex. This data indicates whether and when intrinsic events occur, their duration and morphology. The timing of certain events (or their failure to occur when expected) is used to trigger various device actions. For example, sensing an atrial depolarization may begin a timer (an escape interval) that leads to a ventricular pacing pulse upon expiration. In this manner, the ventricular pacing pulse is coordinated with respect to the atrial event.

The heart includes four chambers; specifically a right and a left atrium and a right and left ventricle. Leads are commonly and routinely placed into the right atrium as well as the right ventricle. For left sided applications, the lead is typical guided through the coronary sinus and into a cardiac vein. One or more electrodes are then positioned (within the vein) to contact an outer wall of the left atrium and/or left ventricle. While direct access to the interior of the left atrium and left ventricle is possible, it is generally less preferable. As the left ventricle provides oxygenated blood throughout the body, any foreign object disposed on the left side could lead to the formation of clots and would increase the risk that such a clot would form and be dispersed.

The sensing and utilization of electrical data is commonly employed as the electrodes used for delivering stimulus are typically also useful in sensing this data. This is generally non-problematic in left-sided applications as the electrical waveform is adequately sensed from the above described left side lead placement position.

A wide variety of other sensors are employed to sense parameters in and around the heart. For example, flow rates, oxygenation, temperature and pressure are examples of parameters that provide useful data in certain applications. Obtaining such data on the right side is typically non-problematic; however, obtaining the same data directly from the left side is made more difficult by the general inability (or undesirability) to place a sensor or component into the left atrium or ventricle.

Pressure data, in particular, is a useful parameter in determining the presence, status and progression of heart failure. Heart failure often leads to an enlargement of the heart, disproportionately affecting the left side. Left side pressure values would be useful in monitoring the patient's condition; gauging the effectiveness of a given therapy such as Cardiac Resynchronization Therapy (CRT); and timing, controlling or modifying various therapies. Of course, the direct measurement of left sided pressure values is made difficult because pressure sensors generally are not implanted within the left atrium or left ventricle.

Left atrial pressure, in particular, is a variable that defines the status of heart failure in a patient. Attempts have been made to measure surrogates of this variable by monitoring pulmonary wedge pressure in clinical care. Measurement of ePAD with implantable devices such as the Medtronic Chronicle™ have been used to measure real-time intracardiac chamber pressure in the right ventricle and provide an estimate of mean left sided pressure. These techniques generally do not provide certain phasic information and do not necessarily correlate with left atrial pressures under certain conditions such as pulmonary hypertension or intense levels of exercise.

DETAILED DESCRIPTION

Figure 1:
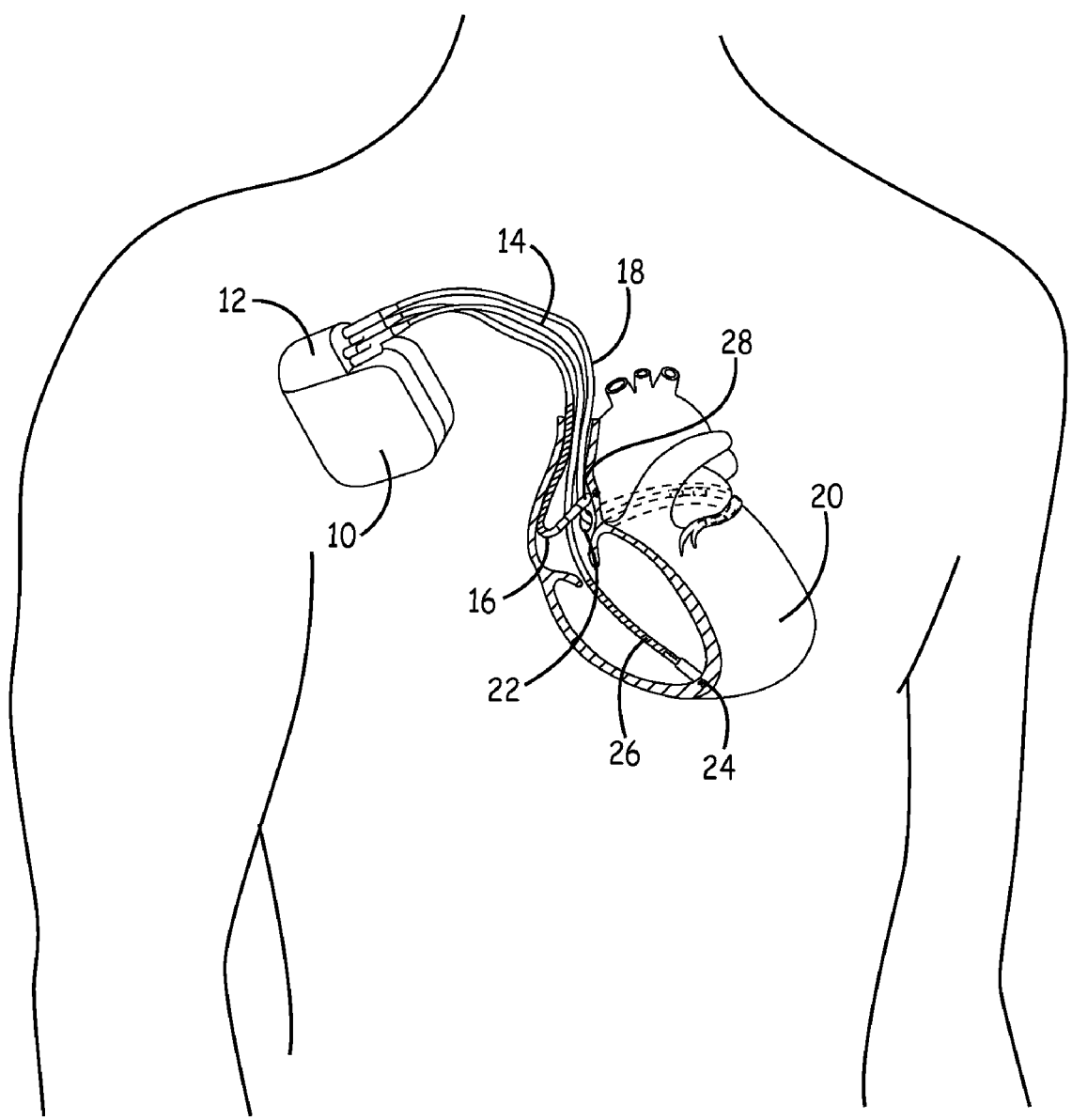
FIG. 1 illustrates an implantable medical device (IMD) having a plurality of leads implanted within a heart.

FIG. 1 illustrates an implantable medical device (IMD) 10 that includes pacing, cardioversion and defibrillation capabilities. A header block 12 forms a portion of the IMD 10 and three leads 14, 16, 18 are illustrated as coupled with the header block. A right ventricular lead 14 is disposed in the right ventricle of the heart 20. More specifically, a helical electrode tip 24 is embedded into the apex of the right ventricle. The electrode tip 24 forms or is part of a tip electrode and a coil electrode 26 is also included. A ring electrode may be disposed between the tip electrode 24 and the coil electrode 26.

An atrial lead 16 is disposed within the right atrium such than an electrode 28 contacts an interior wall of the right atrium. A left sided lead 18 is illustrated as passing through the coronary sinus 22 and into a cardiac vein. In this position, the left sided lead 18 has a distal end in contact with an outer wall of the left ventricle. The IMD 10 includes a housing that can act as an electrode or, though not illustrated, may include multiple electrodes. With such a configuration pacing stimuli is selectively delivered to the right atrium, the right ventricle, and/or the left ventricle. Likewise, a defibrillation pulse may be generated from any given electrode to any second electrode, such that the defibrillation waveform traverses the desired portion of the heart 20.

Figure 2:
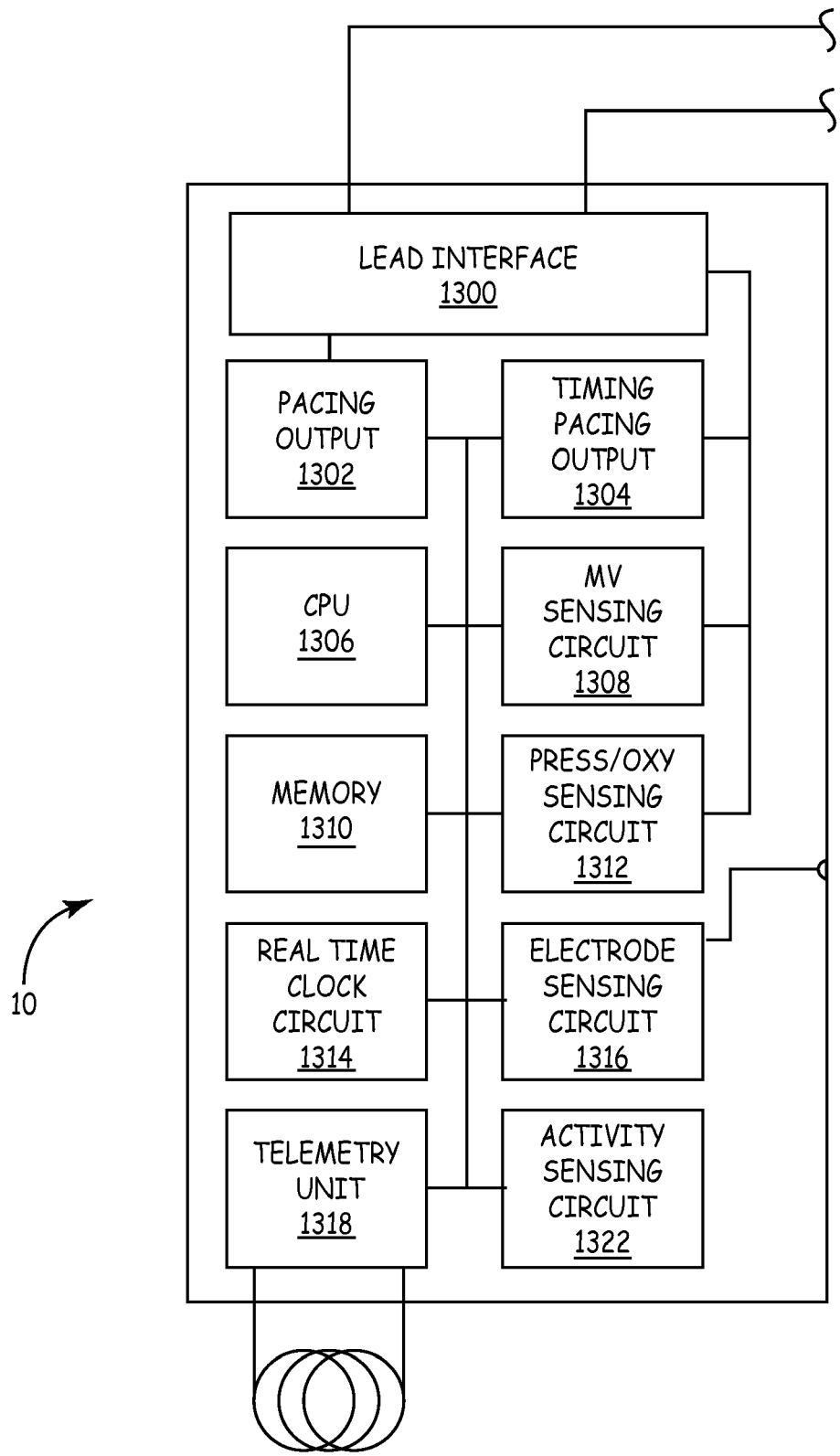
FIG. 2 is a block diagram illustrating the functional components of an IMD.

FIG. 2 is a simplified schematic diagram illustrating certain components of the IMD 10. The IMD 10 includes a processor or CPU 1306, memory 1310, timing circuits 1314, timing output circuit 1304, pacing and defibrillation output circuits 1302, an appropriate lead interface 300, and appropriate electrode sensing circuits 1316. The operation of the IMD 10 may be controlled by software or firmware and may be reprogrammed and/or provide data to an external device via telemetry unit 1318.

Also illustrated are exemplary sensing units that may be included with IMD 10. For example, an activity sensing circuit 322, and a minute ventilation circuit 1308 are included. Thus far, IMD 10 is illustrated in an exemplary manner and may or may not include all components illustrated and may include many additional components and capabilities without departing from the spirit and scope of the present invention.

A pressure sensing circuit 1312 receives input from the pressure sensor described herein. In one embodiment, a pressure sensor is included on the right atrial lead 16. The pressure data, when received, is used by the CPU 1306 to monitor or control therapy, monitor the status of the heart, and/or to provide information to an external device via telemetry unit 1318. It should also be appreciated that various pressure sensors may provide relative data and an absolute pressure sensor (not shown) may be positioned external to the heart and utilized to provide reference data via telemetry unit 18 and/or to the external device.

Figure 3:
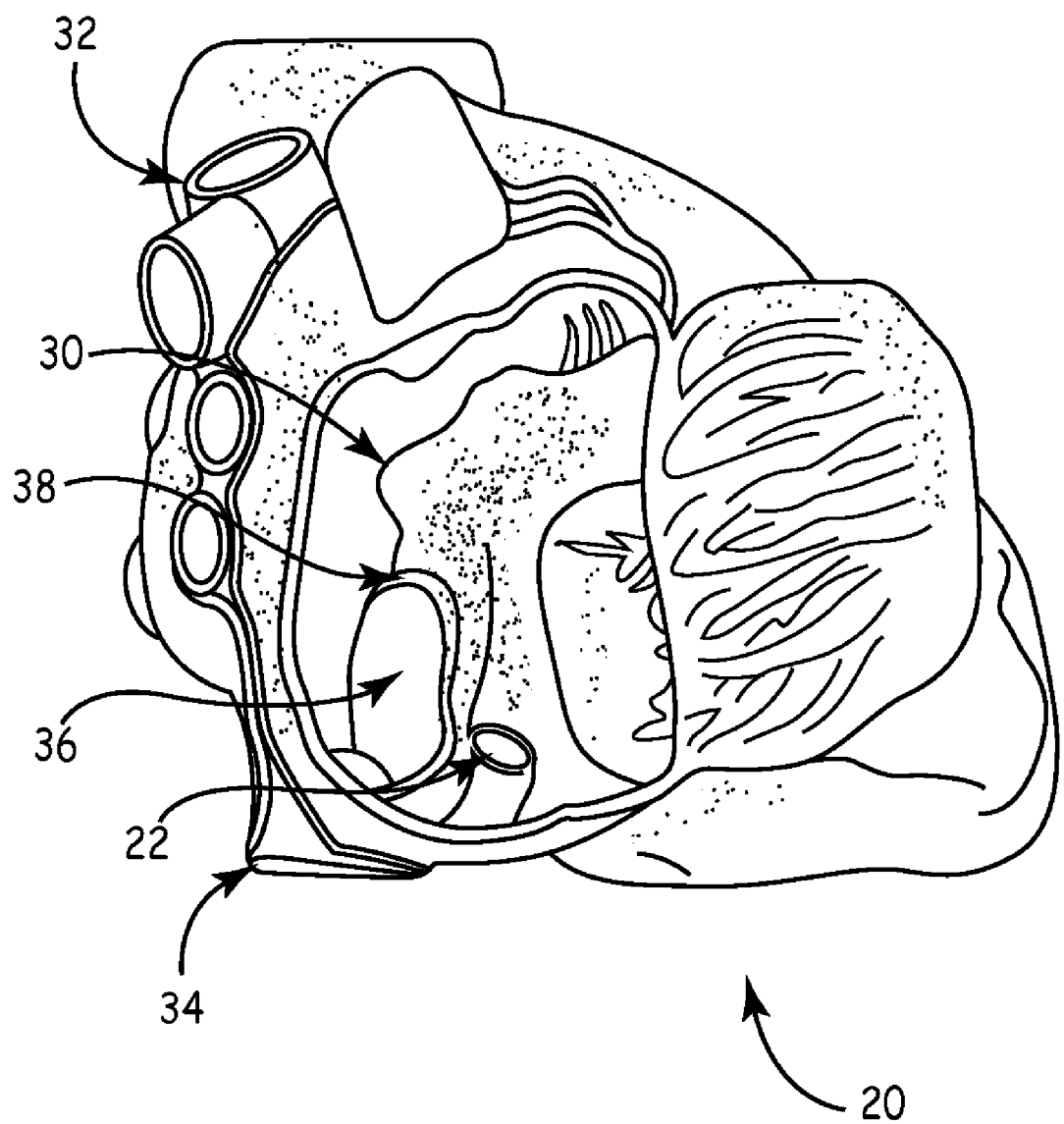
FIG. 3 is an illustration of a heart showing an interior view of a right atrium and indicating the location of the fossa ovalis.

FIG. 3 is an illustration of the anatomy of a human heart 20. In particular, the interior of right atrium 30 is illustrated, along with the superior vena cava 32 and inferior vena cava 34. The atrial septum, dividing the right atrium from the left atrium is primarily defined (from the right side perspective, by the fossa ovalis 36. Surrounding the fossa ovalis 36 is the fossa limbus 38, which is a raised muscular rim. The fossa ovalis 36 is a relatively thin, but very strong membrane that separates the right atrium from the left atrium and is a non-conductive pathway for depolarization. The fossa ovalis 36 marks the previous location of the foramen ovale, which in embryonic and fetal development provided for direct passage between the atrial chambers. The fossa limbus 38 and the atrial tissue surrounding the fossa limbus 38 is conductive.

Figure 4A:
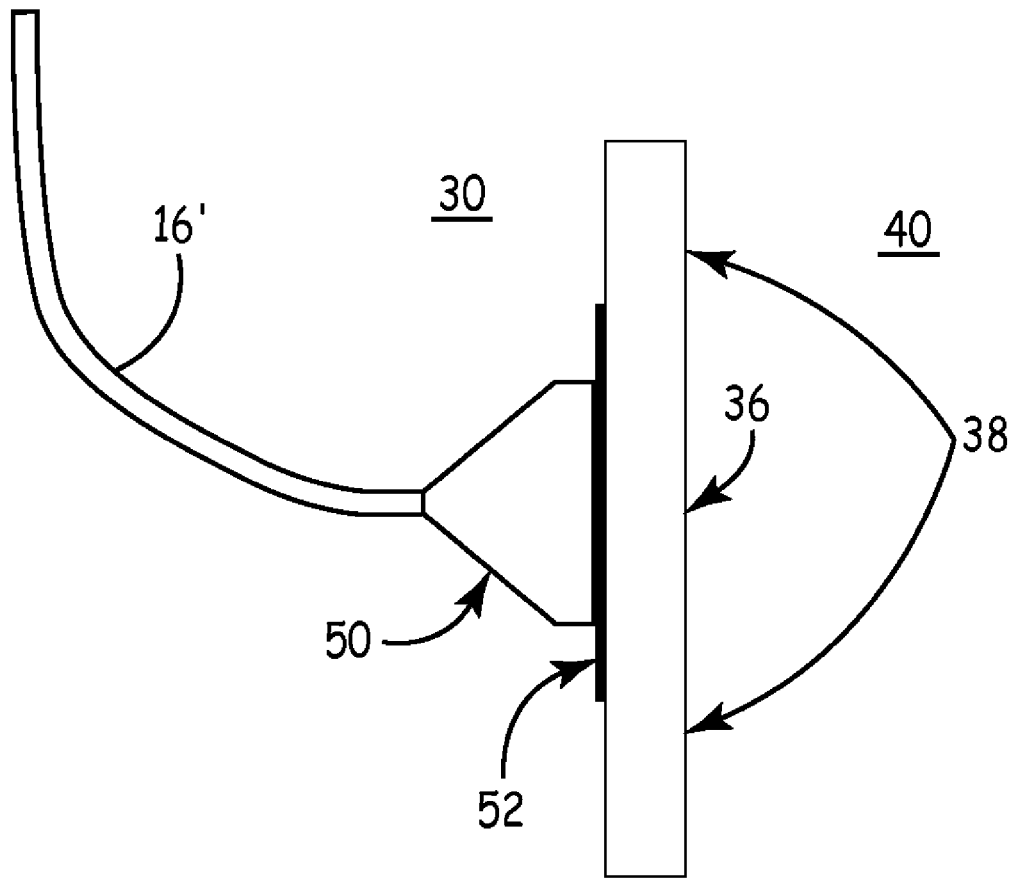
FIGS. 4A-4D are schematic diagrams illustrating an embodiment of a pressure sensor assembly having deployable anchor prongs.

FIG. 4A is a schematic illustration of a pressure sensor assembly 50 coupled with the atrial lead 16'. The pressure sensor assembly 50 is disposed within the right atrium 30 and its position relative to the left atrium 40 is illustrated. More specifically, the pressure sensor assembly 50 is in contact with the fossa ovalis 36 and in this embodiment, held in place through the use of deployable anchoring prongs 52. The anchoring prongs 52 may also serve as electrodes to pace and/or sense within the right atrium 30. In this manner, the pressure sensor assembly 50 utilizes the fossa ovalis 36 as a portion of a pressure sensing configuration to measure the left atrial pressure from within the right atrium 30. That is, by controlling for the effects of the right atrial pressure, the membrane of the fossa ovalis 36 (or a portion thereof) will deflect proportionally to the fluid pressure exerted in the left atrium 40 and provide direct, real time pressure indications. These pressure indications will provide relative pressure values as well as pressure changes (deltas) and dynamic waveform morphologies. With the inclusion of an external pressure reference sensor, such values could also be correlated to absolute pressure values.

Figure 4B:
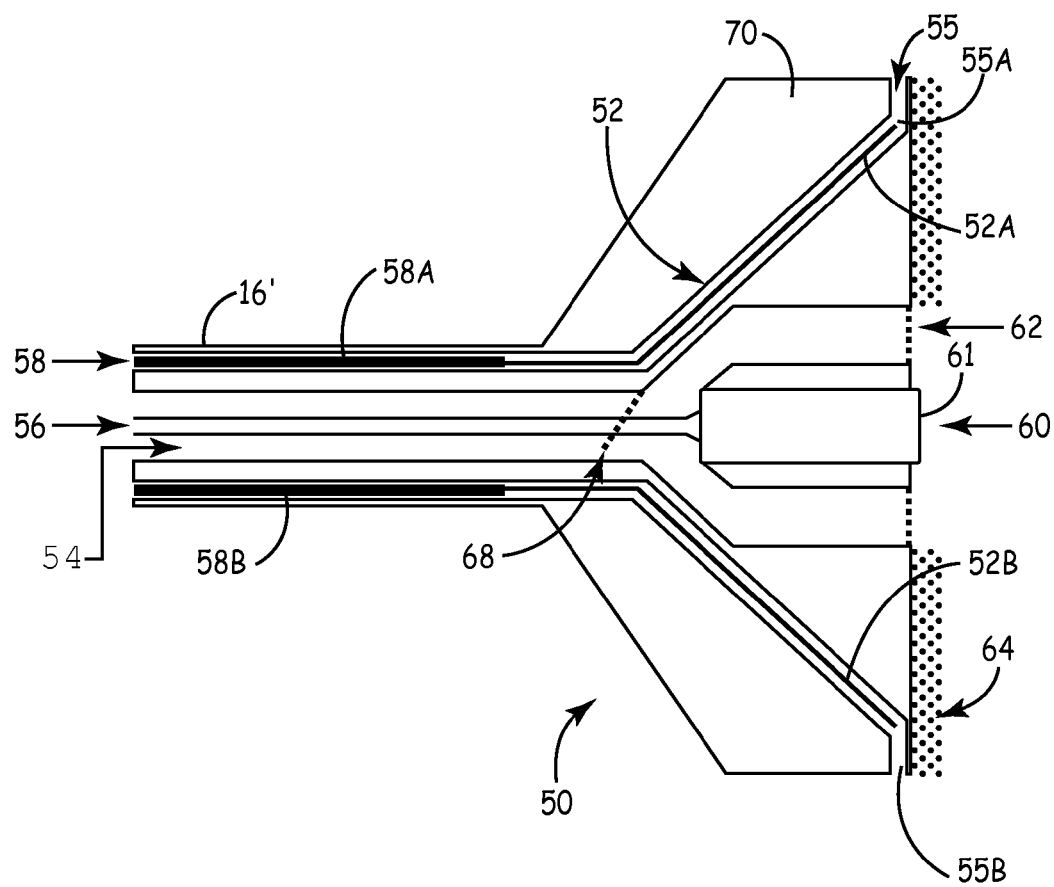

FIG. 4B is a schematic side sectional view of the pressure sensor assembly 50. The assembly 50 includes a housing 70 that is coupled with the lead 16'. Disposed within the housing 70 are one or more anchor prong tracks 55, with track 55a, 55b illustrated. In this embodiment, there are a total of four such tracks each having a corresponding anchor prong 52, with prongs 52a and 52b illustrated. Coupled or contacting a proximal portion of each anchor prong 52 is a prong deployment mechanism 58. The prong deployment mechanism 58 deploys or retracts the anchor prong 52 along the anchor prong tract 55 from the proximal end of the lead 16'. Because the housing 70 contacts the fossa ovalis 36, the anchor prong tracts 55 direct the anchor prongs into the tissue of the fossa limbus 38. As the shape of the fossa ovalis 38 and correspondingly the fossa limbus 38 will vary from patient to patient, the distance from any given prong tract 55 to limbus tissue may vary. Thus, the anchor prongs 52, in one embodiment, may be independently advanced in varying distances to account for this anatomical variation. Alternatively, the prongs 52 are each made sufficiently long to accommodate wide variations in distance. This may result in a given prong 52 piercing through the limbus 38 and into or along the surrounding atrial tissue. This is non-problematic and provides an even greater area of contact between the prong 52 and conductive tissue. As such, independently advanced prongs 52 should be advanced at least a minimal distance into the limbus to assure anchoring and further advancement is optional, but potentially beneficial both from an anchoring perspective as well as for pacing/sensing capabilities.

The prong deployment mechanism 58 is a relatively stiff member that is directly advanced or retracted to effect deployment or retraction of the prongs 52. Alternatively, the prong deployment mechanism could include a threaded portion such that rotation of the deployment mechanism 58 effects lateral movement and a corresponding advancement or retraction of the prongs 52. In an alternative embodiment, the prong deployment mechanism 58 may be selectively decoupled from the prongs 52.

Figure 5A:
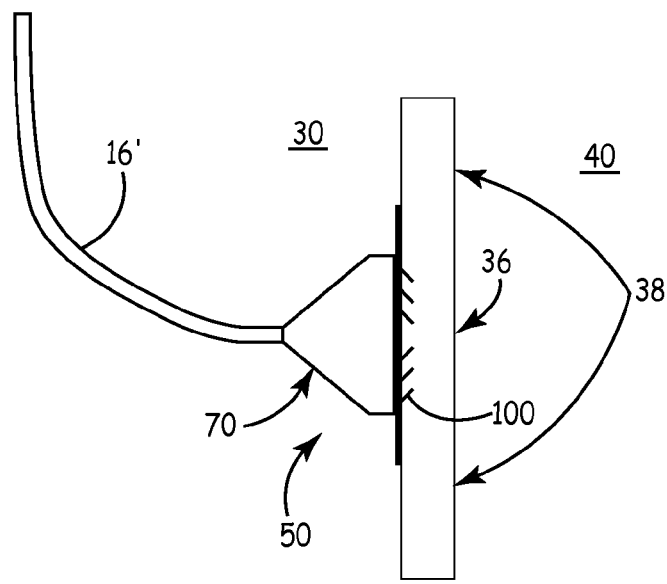
FIGS. 5A-5E are schematic diagrams illustrating an embodiment of a pressure sensor assembly having rotatably deployable anchor prongs.
Figure 5B:
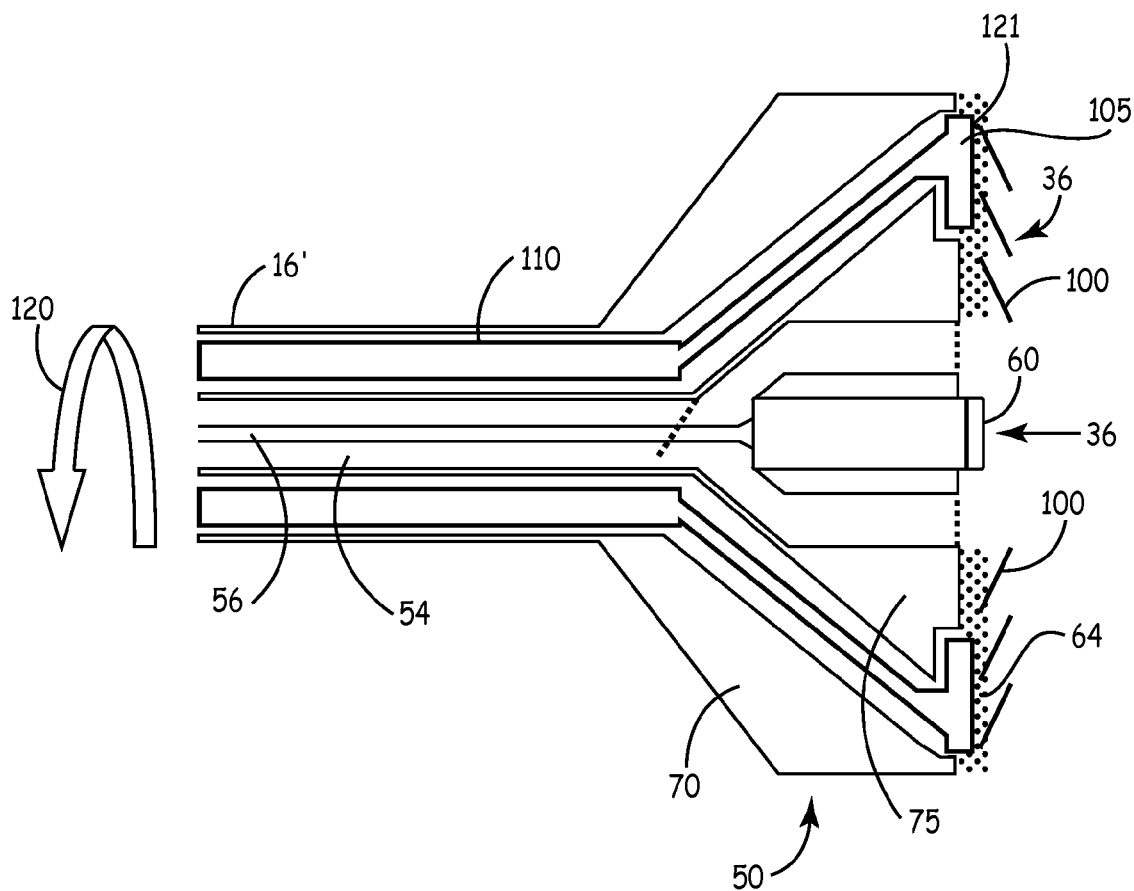
Figure 5C:
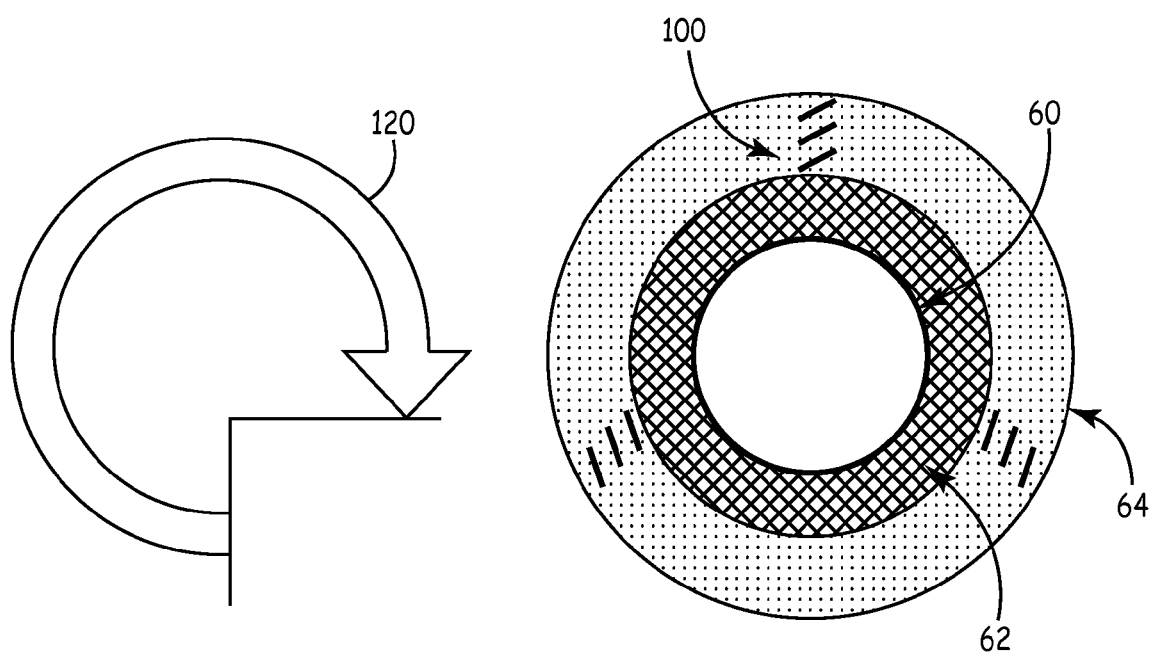
Figure 5D:
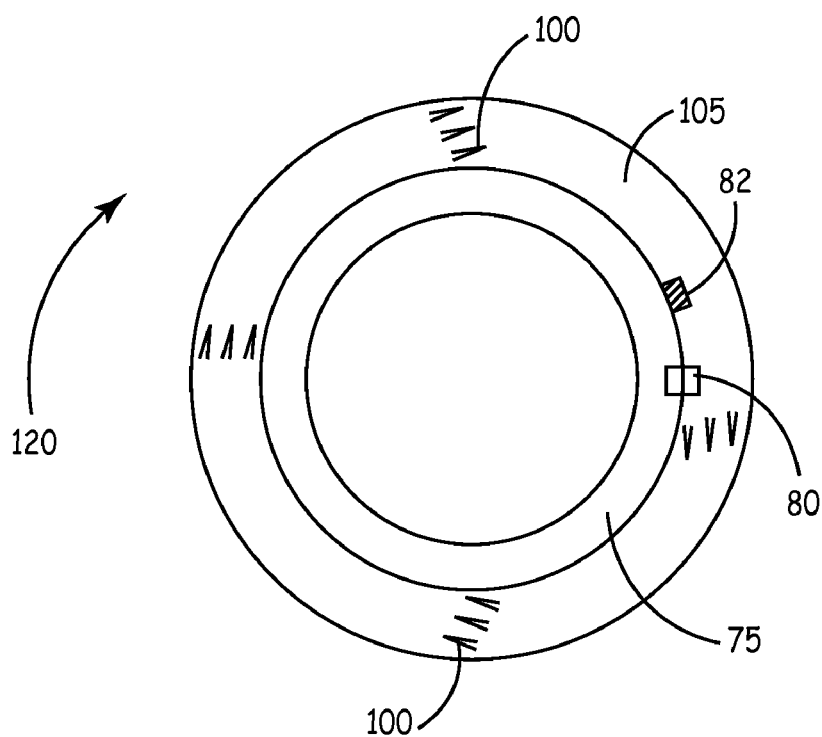
Figure 6A:
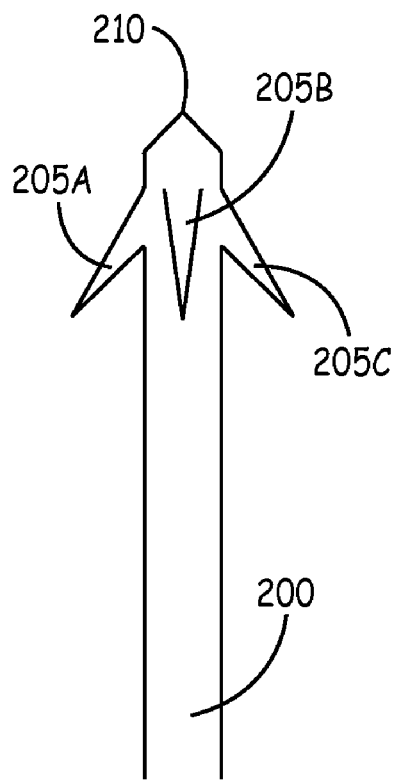
FIGS. 6A-6B illustrate embodiment of anchor prongs.
Figure 6B:
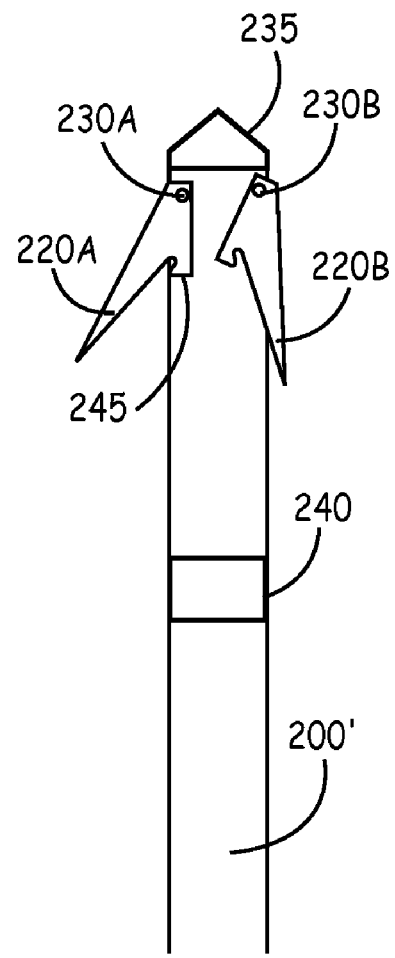

Referring to FIGS. 6A and 6B, two prong embodiments are illustrated. It should be appreciated that the prong embodiments illustrated, those described in the present disclosure and variations thereof are applicable (in any combination) to any of the assembly 50 embodiments disclosed herein. FIG. 6A illustrates prong 200, which may be used, for example, as prong 52 in FIGS. 5A-5D. Prong 200 includes a distal piercing tip 210 as well as a plurality of fixed tines 205a-205c. Thus, forward advancement of prong 52 is permitted, but retraction is resisted by the fixed tines 205a-205c as they embed themselves within tissue and also serve as locations where tissue encapsulation can occur. FIG. 6B illustrates an alternative prong 200'. Prong 200' also includes a distal piercing tip 235. Two pivoting tines 220a and 220b are illustrated as being pivotable about pivot point 230a and 230b respectively. With the tine 220b in the retracted position, forward advancement is facilitated. Withdrawal of the prong 200' (e.g., pulling backwards during implantation) will cause the tines 220 to deploy to the extended position as tine 220a is illustrated. While not separately shown, a push rod, guidewire or similar device could be coupled with a stop block 245 of the tine 220 so that it may be moved from the extended position to the retracted position from the proximal end of lead 16'. In this manner, the prong 200' could be removed or repositioned after an initial implant. Tine 220b is illustrated as partially protruding in the retracted position to facilitate deployment and it should be appreciated that the tine 220b could be fully retracted within prong 200' for removal, withdrawal or repositioning.

Prong 200' also schematically illustrates a first electrode 240 disposed along the main shaft. Piercing tip 235 is also indicated to be an electrode. Multiple electrodes may be separately disposed along prong 200' or the entire prong 200' may serve as a single electrode.

Referring to FIGS. 4A-4D, a pressure sensor 60 is centrally disposed within the housing 70 and is communicatively coupled with the IMD 10 via communication line 56. Of course, various communication protocols, including wireless protocols may be utilized. In such an embodiment, communication line 56 would represent an antenna structure. Intracardiac pressure sensing may be accomplished in a number of ways. The following U.S. patents disclose a variety of pressure sensors and are herein incorporated by reference in their entireties: U.S. Pat. Nos. 6,223,081; 6,221,024; 6,171,252; 6,152,885; 5,919,221; 5,843,135; 5,368,040; 5,353,800; and 4,967,755. In the illustrated example, pressure sensor 60 includes a high fidelity pressure transducer mounted on a distal end of a capsule and in direct contact with the fossa ovalis 36, upon implant.

Phasic information of the left atrial pressure provided by the pressure sensor 60 can be used, for example, by the IMD 10 to control several pacing parameters such as AV timing and VV timing for management of AF and CHF by optimizing left sided filling and ejection cycles and enhance cardiovascular hemodynamic performance. Such data may also be used for assessment of mitral regurgitation and stenosis. For device based management of atrial fibrillation, the phasic information can be used for discriminating atrial fibrillation from flutter and optimizing atrial anti-tachycardia pacing therapies.

Implantable pressure sensor 60 provides diagnostic data to clinicians and/or control device operation by automated feedback control. Direct, real-time left atrial pressure measurement may be utilized to provide diagnostic information for management of heart failure and in patients with pacemakers, to optimize pacing parameters to prevent its progression. In addition, pressure sensor 60 provides information about the atrial substrate for management of AF and may control pacing parameters to prevent progression of AF. Reference is made to U.S. patent application Ser. No. 11/097,408, filed on Mar. 31, 2005 and titled "System and Method for Controlling Implantable Medical Device Parameters in Response to Atrial Pressure Attributes," which is herein incorporated by reference in its entirety.

Figure 4C:
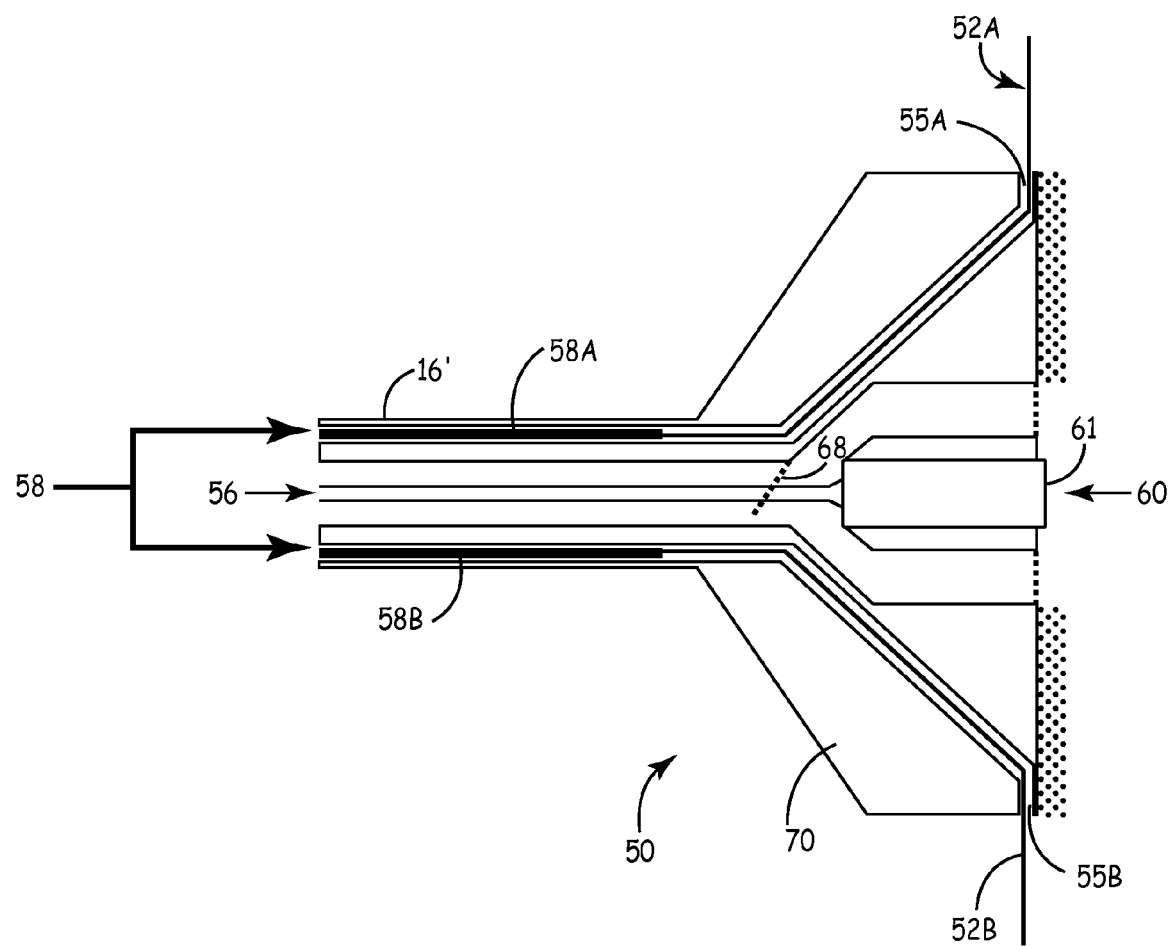
Figure 4D:
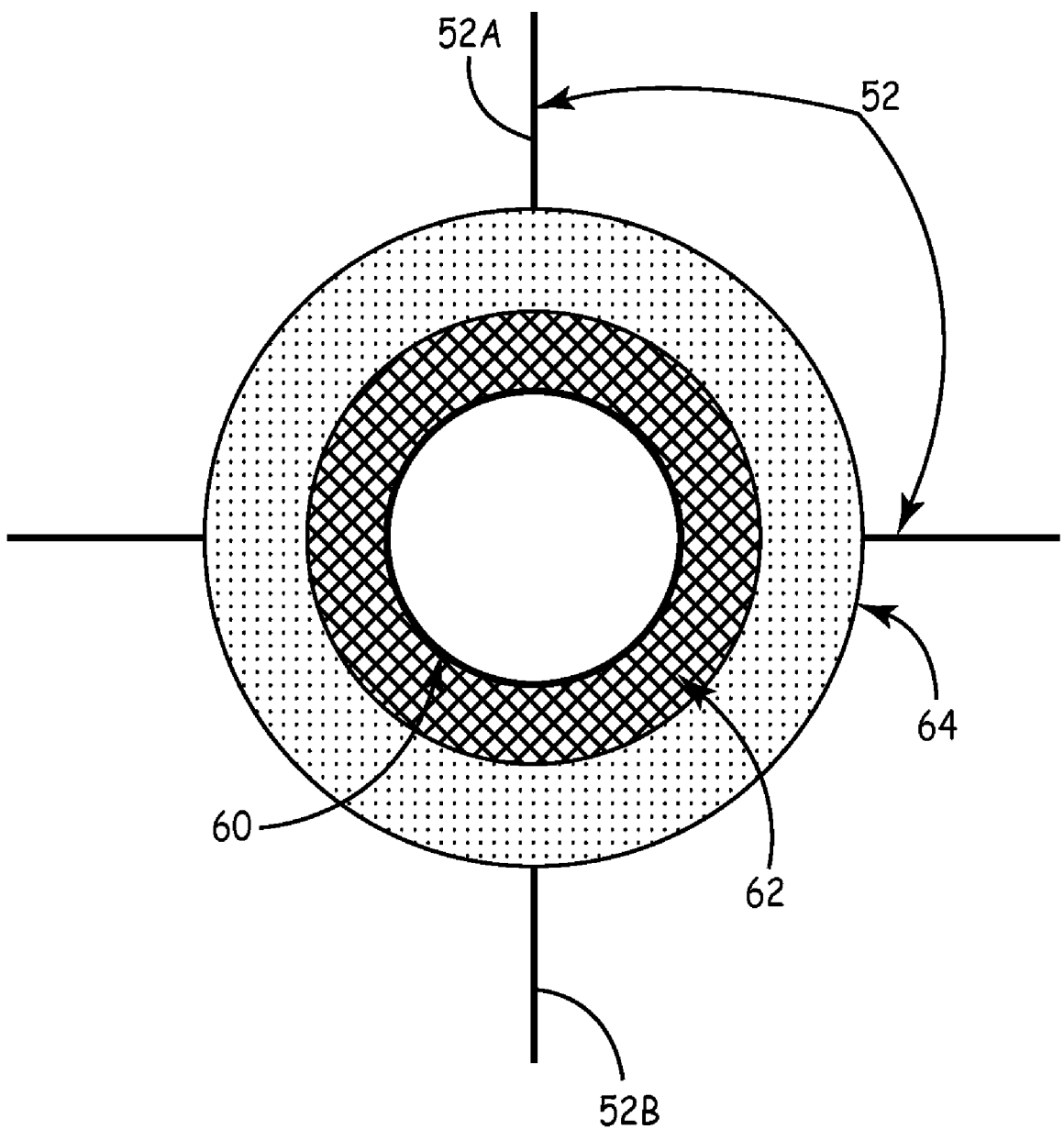

With reference to FIGS. 4B and 4D, an abrasive ring 64 is concentrically disposed about an outer perimeter section of the distal face of the housing 70. The abrasive ring 64 is in contact with ovalis tissue when implanted and stimulates the growth of endothelial or fibrotic structure to further secure the housing 70 to the specified cardiac anatomy. In other words, the ring 64 irritates or otherwise promotes tissue growth that captures and secures at least a portion of the ring 64.

With reference to FIGS. 4B, 4C, and 4D a vacuum channel 54 is provided within the lead 16' and housing 70 that terminates at a vacuum channel grid 62. Disposed within the housing 70 and along the vacuum channel 54 is a check valve 68. During implantation, the housing 70 is maneuvered into position; this generally means that the pressure sensor 60 and/or the housing 70 is placed into contact with the center of the fossa ovalis 36. The housing 70 is firmly held against the fossa ovalis 36. Negative pressure is generated within the vacuum channel 54, for example by drawing a syringe coupled with a proximal access to the vacuum channel 54 disposed near a proximal end of lead 16'. As the negative pressure is generated, the tissue of the fossa ovalis 36 is drawn against the vacuum channel grid 62.

The source of negative pressure may be released and the check valve 68 will close and maintain the vacuum generated. This is optional, as the source of negative pressure may be maintained throughout implant. Once the housing 70 is secured against the fossa ovalis 36, the anchor prongs 52 are deployed and pierce the fossa limbus 38; anchoring the assembly 50 into position. Over time, tissue growth in and around the abrasive ring 64, the vacuum channel grid 62 and the prongs 52 further secure the placement of the sensor assembly 50. Various external techniques may be utilized to determine that proper implantation has occurred such as fluoroscopy, X-ray, CAT scan, MRI or the like. In addition, the data obtained from the prong electrodes 52 and/or the pressure sensor 60 can be used to determine if proper implantation has been achieved.

Once implanted, the prongs 52 may be used as pace/sense electrodes or simply relied upon for anchoring. The pressure sensor 60 will immediately be able to provide data; however, until the above mentioned tissue growth occurs as well as any encapsulation about the pressure sensor 60 itself occurs, the data will change (relatively) over time. That is, the fossa ovalis 36 is acting as a transducing membrane and the resulting signal output will attenuate as this membrane changes in dimension. Once stabilized, the pressure data will be most accurate. The timing of this tissue growth is patient dependant and may take a few days to a few weeks to complete. Of course, when such variation is accounted for, the pressure data may still provide useful data even during this period of time.

The vacuum channel 56 and/or the check valve 68 are optional and may be left out of various embodiments. That is, the housing 70 may be maintained in position against the fossa ovalis 36 by various other means, including manipulation of the lead 16' so that the prongs 52 are deployable. In addition, four anchor prongs 52 and corresponding anchor prong tracts 55 have been illustrated. More or fewer may be utilized. The anchor prong 52 itself is schematically illustrated as being a linear member, but may include fixed or expandable barbs, hooks, other attachment members and may be deformable from the linear configuration.

As indicated, the availability of, as well as the choice to use, negative pressure to secure the assembly 70 during implantation is an option for various embodiments. Likewise, the presence of a check valve 68 is another optional feature. When present and utilized, the check valve 68 will close and maintain negative pressure within the vacuum channel 54 distal to the check valve 68. Over time, pressure within this area will increase and stabilize. The time span for this vacuum dissipation will depend upon the magnitude of the initial vacuum generated as well as the effectiveness of the seal naturally formed between the housing 70 and the fossa ovalis 36. To the extent this leads to a slower dissipation, the vacuum effect will further anchor the device during the period of tissue and fibrotic growth.

In an alternative embodiment, the pressure sensor 60 is separable from the housing 70. The housing 70 is implanted as described either with or without a pressure sensor 60 in place. The pressure sensor 60 is advanced within the lead 16' and secured in its targeted position. This alternative would permit the replacement of the pressure sensor 60 without requiring the removal of the housing 70. As illustrated in later embodiments, the sensor 60 is moveable with a threaded member and corresponding tract. Such a feature may be modified to permit the pressure sensor 60 to be completely separable from the housing 70, as described.

As previously discussed, the fossa ovalis 36 will vary in size and actual shape from one patient to another. Accordingly, flexibility in the deployment distance of the anchor prongs 52 may be provided and/or the anchor prong length is selected to accommodate longer spans, with any excess being beneficial. Alternatively, the sensor assembly 70 may be manufactured in a variety of standard sizes and/or shapes (e.g., circular, elliptical, etc.). The patient's actual fossa ovalis 36 is evaluated and the most appropriate size and/or shape of the standardized sensor assemblies 70 is chosen. Finally, custom sensor assemblies 70 may be made based upon a specific patient's anatomical parameters.

FIGS. 5A to 5D illustrate an alternative embodiment, wherein like numerals are used to denote similar structure to that previously described. In this embodiment, a prong support structure 105 is rotatably coupled within the housing 70. At least one, but preferably a plurality of anchor prongs 100 are coupled with the prong support structure. The anchor prongs 100 are positioned at a non-orthogonal angle to the prong support 105. The particular angle chosen may vary; however, the various anchor prongs 100 should be directionally aligned. That is, they should all angle in the same direction when viewed in a like manner from the frame of reference defined by the central point of the sensor 60.

In use, the sensor assembly 70 is positioned against the fossa ovalis 36. Negative pressure may be utilized to secure the assembly into place. A prong support rotation mechanism 110 is coupled to the prong support 105. The prong support rotation mechanism 110 is rotated in the direction of arrow 120. This action causes the prong support 105 to rotate and likewise cause the anchor prongs 100 to rotate. Due to the angle the anchor prongs 100 are positioned at, this rotation causes the anchor prongs 100 to pierce and enter the tissue of the fossa ovalis 36, pulling the housing 70 towards the tissue as rotation continues. Thus, a different angular orientation of anchor prongs 100 may result in the advancing rotational direction to be the opposite of that illustrated. As most clearly illustrated in FIG. 5B, this angular piercing secures the sensor assembly 70 against the fossa ovalis 36. Again, over time tissue growth and encapsulation occurs further securing the assembly 70. Though not shown in detail, appropriate slots are provided within the abrasive ring 64 to permit the travel of the prongs 100. Alternatively, the abrasive ring 64 is absent in relevant section or is constructed of such a material as to permit the travel of the prongs 100.

When implanted as illustrated, the anchor prongs 100 preclude separation of the assembly 70 from the fossa ovalis 36. The more acute the angle of the prongs 100 with respect to the major plane of the fossa ovalis 36, the more secure the attachment will be, within reason. If the prong support rotation mechanism 110 were rotated in a direction opposite that indicated by arrow 120, then the anchor prongs 100 would disengage the fossa ovalis 36. Absent sufficient tissue growth and/or the presence of a sufficient vacuum (or other deliberate means), the sensor assembly 70 would separate from the fossa ovalis 36. This is advantageous during implantation in that the sensor assembly 70 may be repositioned with relative ease.

Once implantation is complete, such separation is undesirable and unintentional reverse rotation of prong support rotation mechanism 110 is precluded. In order to prevent such reverse rotation, the present invention provides for numerous anti-reverse rotation mechanisms that may be used alone or in any combination. The anti-reverse rotation mechanism, in general, precludes or hinders reverse rotation to a sufficient degree so that the sensor assembly 50 is reasonably and reliably secured to the fossa ovalis 36 by the anchor prongs 100 alone. In one embodiment, anti-reverse rotation mechanism is disposed in the proximal end (not illustrated) of the prong support rotation mechanism 110 and includes a locking mechanism that is selectively engaged to fix the prong support rotation mechanism 110 relative to the lead body 16'. Another anti-reverse rotation mechanism would include one or more of the anchor prongs 100 having a barb, hook, or other anchoring feature that precludes or hinders withdrawal of the anchor prong 100 from the tissue of the fossa ovalis 36 (e.g. FIGS. 6a-6b). Though not illustrated, one or more anchor prongs 52 (FIG. 4b) may be used in addition to the angular anchor prongs 100 to provide flexibility during implantation. That is, the rotational movement causes anchor prongs 100 to engage and when satisfied with placement, an anchor prong 52 including a barb or hook would be deployed to prevent reverse rotation (and to serve as an electrode, if desired).

Another anti-rotation mechanism is a friction lock. That is, the tolerances between the prong support 105 and one or more portions of the assembly 70 are such that frictional forces make rotation difficult. Depending upon how much force is required, this could make intentional rotation during implantation more difficult; particularly when considering that the rotational force or torque applied is transferred along a flexible member having the same length as lead body 16'. An appropriate lubricant may be initially provided to ease rotation. For example, the friction lock may occur at the interface 121 between the prong support 105 and the fossa abrasive ring 64. A biocompatible lubricant would be provided at the interface 121 and the lubricant would break down upon exposure to bodily fluids over an appropriate time interval.

Figure 5E:
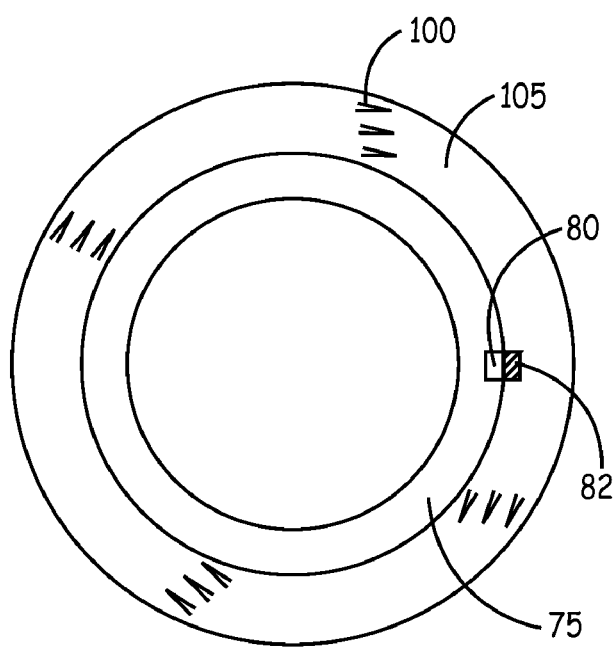

A locking tab, detent or other mechanical member may be provided as an anti-rotation mechanism. That is, when the prong support rotation member 110 is fully rotated the mechanical member is engaged and prevents reverse rotation. Thus, during implantation, the prong support rotation member 110 is not fully rotated until proper placement is confirmed. FIGS. 5D and 5E illustrate one embodiment of utilizing a protruding tab 82 in combination with a detent 80 to prevent reverse rotation. Certain elements of the assembly 50 are not illustrated for purposes of clarity.

FIG. 5D illustrates the prong support 105 and a plurality of prongs 100. A portion of an interior housing support 75 (see also FIG. 5B) is shown relative to the prong support 75. As illustrated, the prong support 105 is forward of the interior housing support 105. The protruding tab 82 extends from a rear surface (as illustrated) of the prong support 105 towards the interior housing support 75. The detent 80 is provided within the interior housing support 75 and is configured to receive the protruding tab 82. FIG. 5D illustrates the prong support 105 prior to complete rotation in the direction of arrow 120. At this point, rotation in either direction is permitted. FIG. 5E illustrate protruding tab 82 engaged within the detent 80. Rotation in either direction is now precluded.

The protruding tab 82 may be a fixed member that abuts the interior housing support 75 and the spring tension of the prong support 105 causes the protruding tab 82 to engage the detent 80. Alternatively, the protruding tab 82 may be a spring loaded member. Finally, the protruding tab 82 may be releasable via a number of mechanisms. In one embodiment, the protruding tab 82 is mechanically retracted by a member operable from a distal end of lead 16'. In another embodiment, the protruding tab 82 and detent 80 are shaped such (e.g., angled wall or walls) that sufficient force may be applied to cause the protruding tab 82 to exit the detent 80. Alternatively, the interior housing support 75 may be moved in a proximal direction, thus separating the tab 82 from the detent 80. It should be readily apparent that a number of alternatives exist that preclude unintentional reverse rotation while providing the option to deliberately remove or reposition the device.

Referring to FIGS. 7A-7D, another embodiment of pressure sensor assembly 50 is illustrated. In this embodiment, a plurality of piercing prongs 300 are illustrated. Specifically, four prongs 300a-300d are disposed about the interior housing support 75. The prongs 300 pierce through the fossa ovalis 36 and secure the housing 70. Each piercing prong 300 is disposed within a prong track 310, with tracks 310a and 310b being illustrated. The prong deployment mechanism 58 (linear, threaded or otherwise) is advanced in the direction of arrow F. This drives the head 315 of the prong 300 through the tissue. More specifically, the head 315 includes a piercing tip 320 and one or more locking tabs 355 that pivot with respect to the main axis of the prong 300. An anchor recoil spring 305 is provided for each prong 300; with recoil springs 305a and 305b illustrated. Thus, deployment of the prong 300 must include sufficient force to overcome the spring tension of the anchor recoil spring 305 and to pierce the relatively strong tissue of the fossa ovalis 36.

Figure 7A:
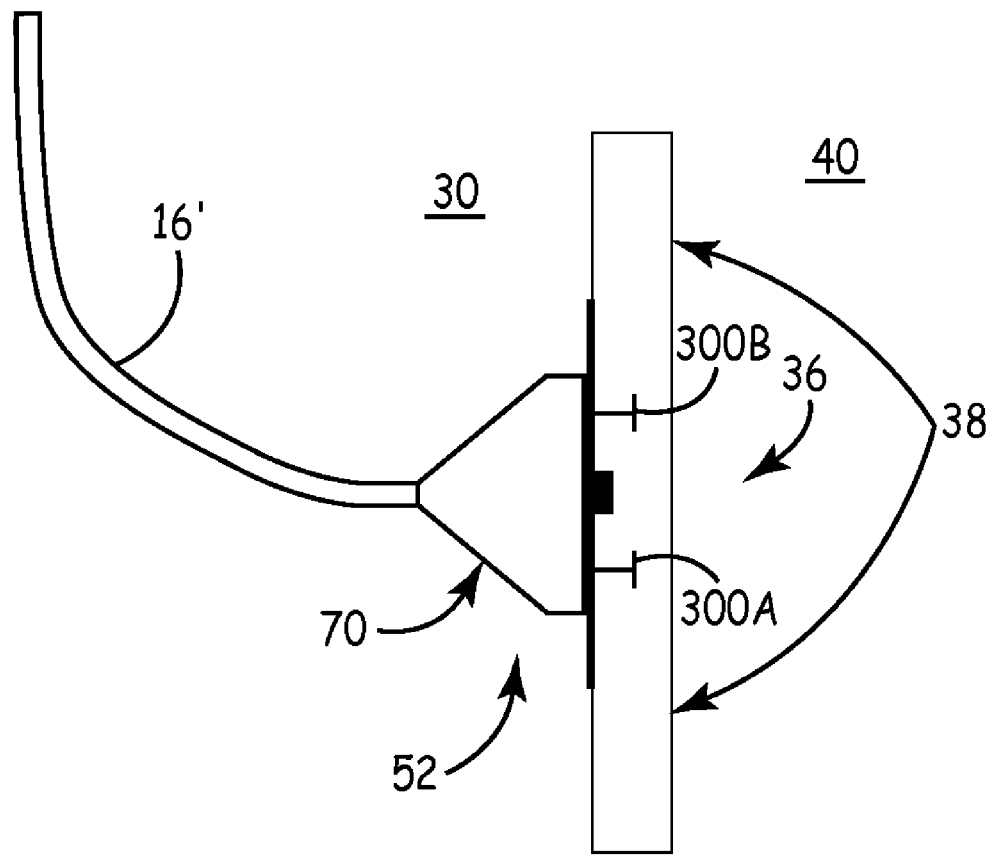
FIGS. 7A-7D are schematic diagrams illustrating an embodiment of a pressure sensor assembly having prongs that pierce through the fossa ovalis.
Figure 7B:
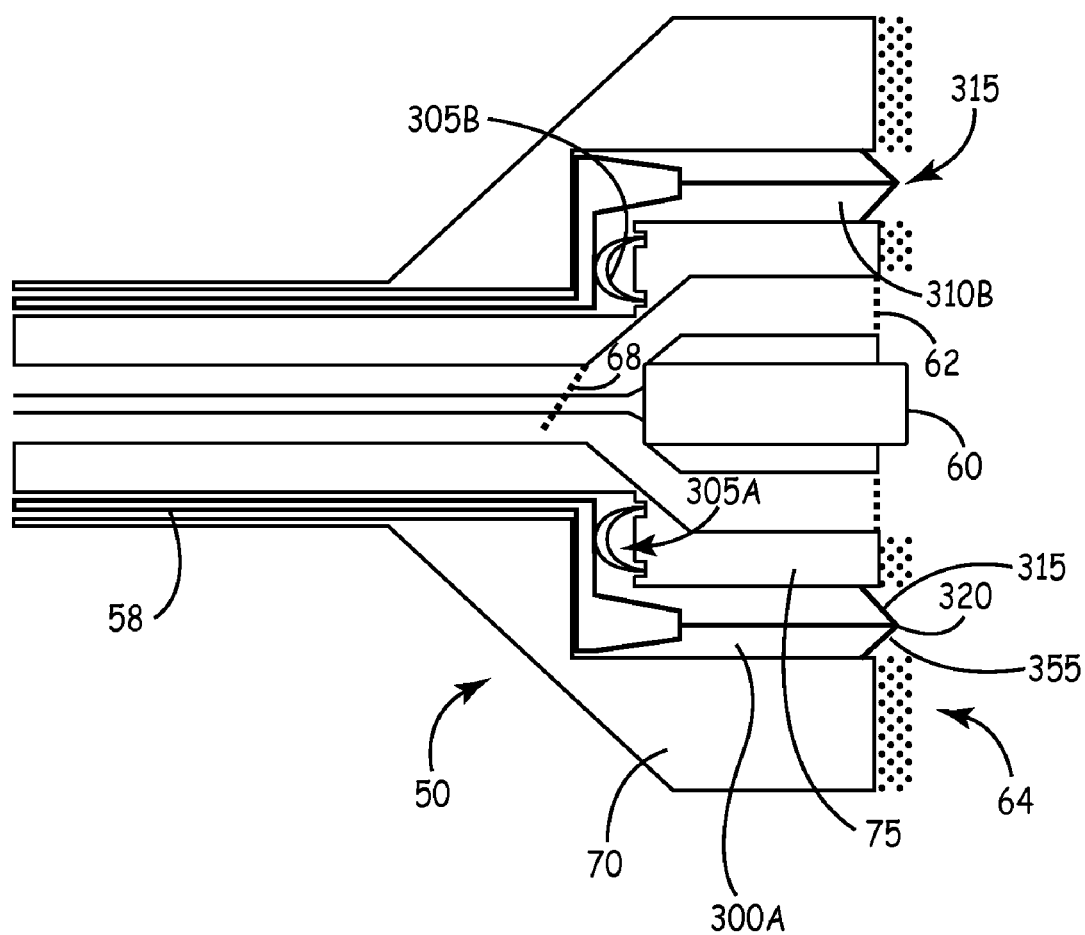
Figure 7C:
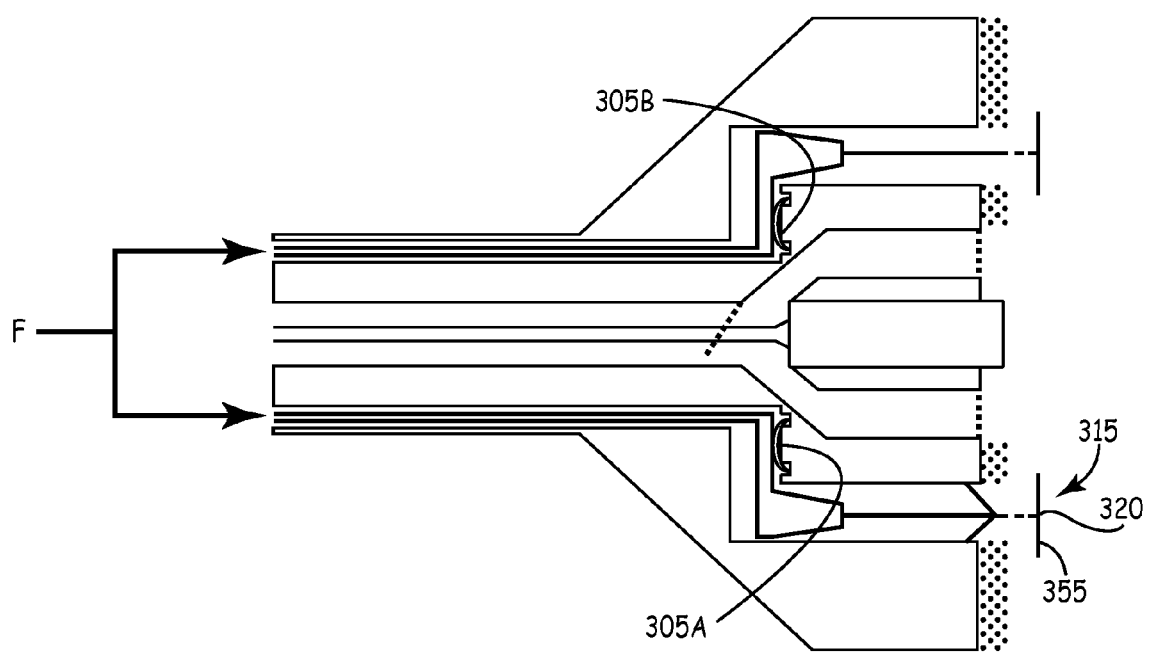
Figure 7D:
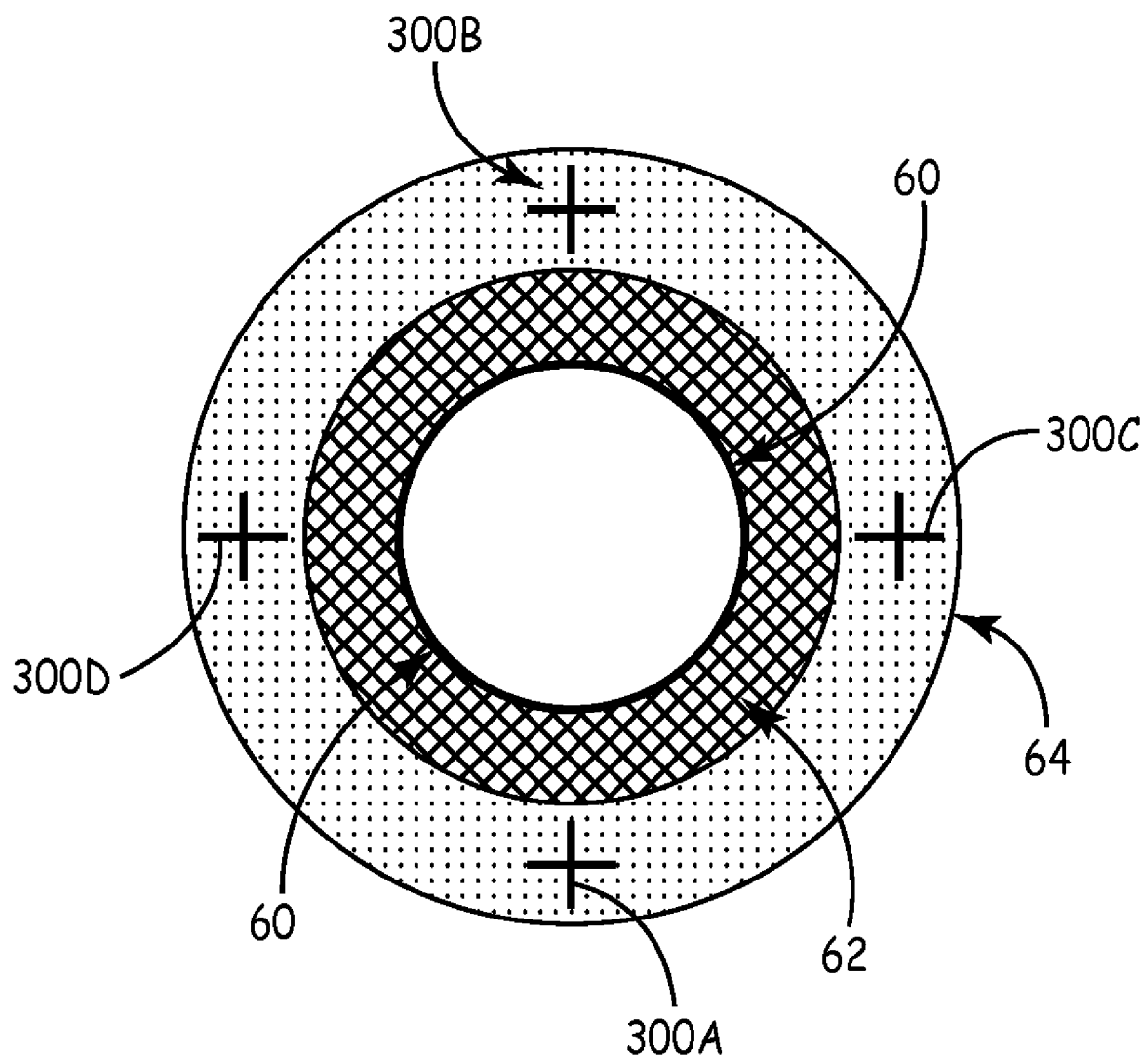

FIG. 7B schematically illustrates the prongs 300 prior to deployment. Anchor recoil springs 305 are either free of tension or as illustrated, retain the prongs 300 in a proximal position. In FIG. 7C, force has been applied in the direction of arrow F. The prongs 300 have pierced the fossa ovalis and the force applied by the prong deployment mechanism 58 is reduced or eliminated. The anchor recoil springs 305 are compressed in the process and consequently, exert a force in a direction opposite that indicated by arrow F. As such, the anchor recoil springs 305 exert this force against the prongs 300, causing them to move in a proximal direction. As the tabs 355 are pivotablly coupled to the prong 300, this movement causes the tabs 355 to engage the tissue of the fossa ovalis 36 surrounding the piercing point and open as shown. In this manner the tabs 355 are anchored against the wall of the fossa ovalis 36 within the left atrium 40. As such, the pressure sensor 60 is maintained in the appropriate position. FIG. 7D illustrates the piercing heads 315 and anchoring tabs 355 for each of the prongs 300a-300d. Because the piercing heads 315 and tabs 355 protrude minimally into the left atrium 40, they will typically not disrupt fluid flow in such a manner as to generate clotting. Furthermore, over time tissue growth will encapsulate the piercing heads 315 and tabs 355 serving both to further anchor the assembly 70 and to obviate the presence of a foreign body in the left atrium. It should be appreciated that the anchor prongs 52 of FIGS. 4A-4D could be utilized in a similar manner. That is, rather than deploying into the fossa limbus, the anchor prongs 52 could deploy into and/or through the fossa ovalis 36 to secure the housing 70. For example, the anchor prong tract 55 (FIG. 4B) could continue linearly rather than angling parallel to the fossa ovalis 36. Alternatively, the housing 70 could be reconfigured such that a portion of the housing 70 is in contact with the fossa limbus 38 so that the above described anchor prong variation pierces the fossa limbus 38. The remainder of the housing 70 would be configured so that contact is still maintained between the sensor 60 and the fossa ovalis or as described below, the sensor 60 is advanced forward of the housing 70 to contact the fossa ovalis 36.

Figure 8A:
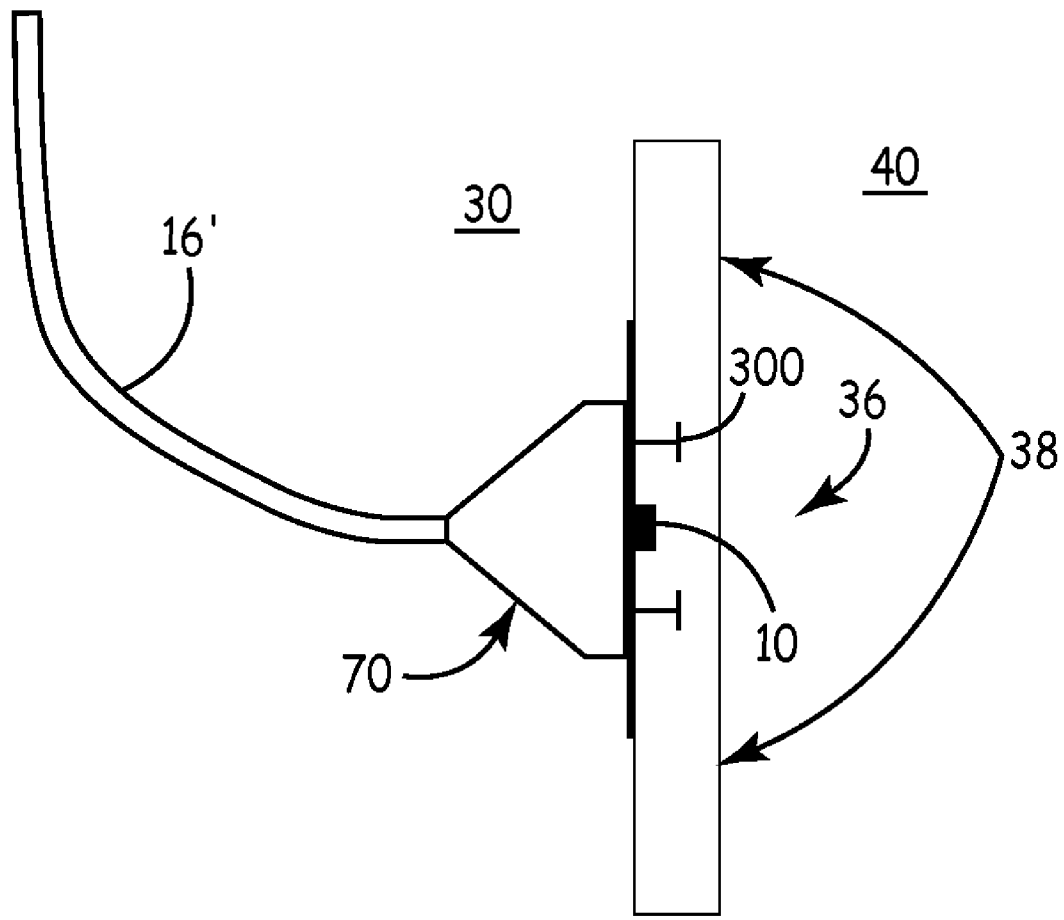
FIGS. 8B-8C illustrate embodiments of a pressure sensor assembly that includes an adjustment mechanism the moves the pressure sensing capsule within the housing.
Figure 8B:
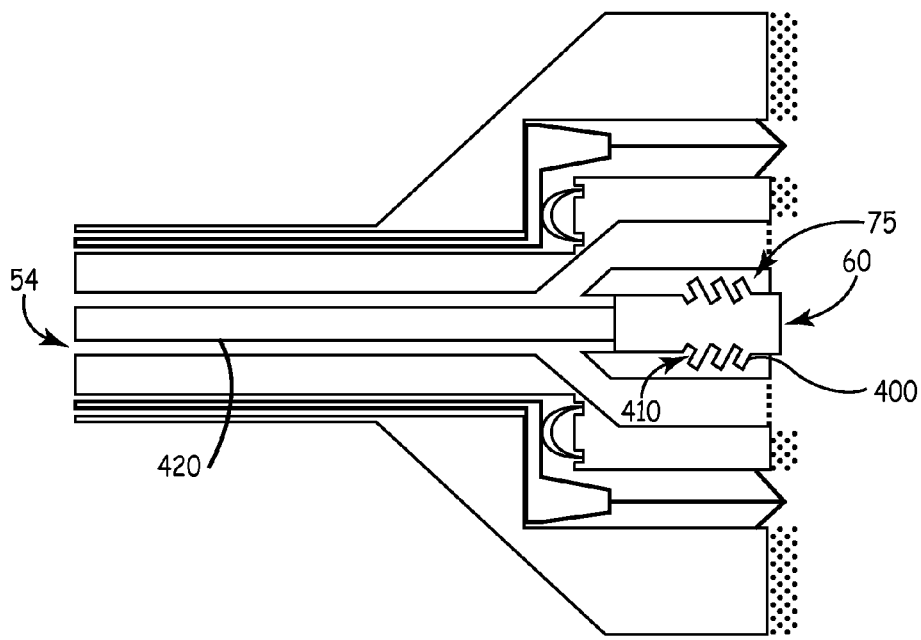
Figure 8C:
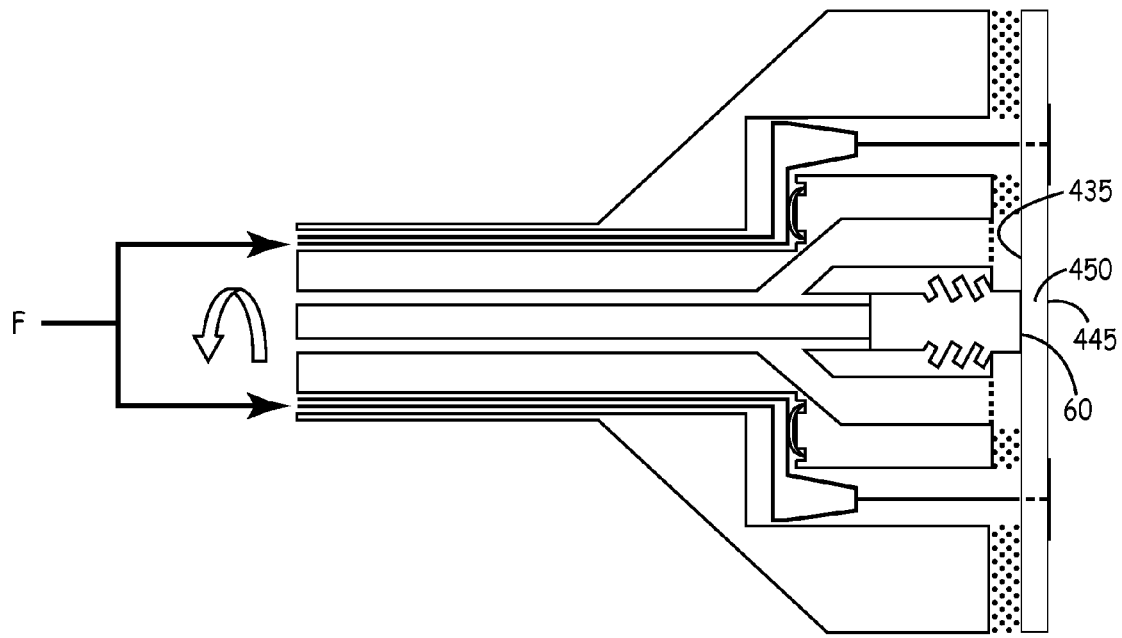

FIGS. 8A-8C illustrate an embodiment of sensor assembly 50 similar to that of FIGS. 7A-7D. In this embodiment, sensor capsule 60 may be advanced and retracted towards and away from the fossa ovalis 36. The movement of the sensor capsule 60 is applicable to any of the embodiment described herein and is not limited with to the embodiment including prongs 300 that pierce into the left atrium 40.

In summary, sensor capsule 60 is advanced and retracted via rotation, which engages a threaded member and translates rotation movement into lateral movement. In the illustrated embodiment, sensor capsule 60 includes a threaded section 400 that engages a corresponding threaded track 410 disposed within the interior housing portion 75. A sensor actuation member 420 is connected to or coupleable with the sensor capsule 60 and permits rotation of the sensor capsule 60 from the proximal end of lead 16'.

FIG. 8B illustrates the sensor capsule 60 in a retracted position and is not in contact with the fossa ovalis 36. As such, a gap 430 is present between the distal end of the pressure sensor capsule 60 and the fossa ovalis 36. The housing 70 may be secured into position using the various embodiments described while this gap 430 is maintained. Subsequently, the sensor actuation member 420 is rotated and the pressure sensor capsule 60 is advanced toward the fossa ovalis 36. The amount of linear travel may be selected based on several considerations. The pressure sensor capsule 60 should traverse the entire gap 430 such that at least minimal contact is made with the tissue of the fossa ovalis 36. In other words, the capsule 60 should contact the right atrial wall 435. Further movement in this direction increases the tension between the sensor capsule 60 and the tissue. Depending upon the particular sensor used, this may result in a better signal output. Continued advancement may cause the capsule 60 to enter the tissue of the fossa ovalis. The pressure sensing capsule may be positioned such that its distal face is disposed along any plane between the right atrial wall 435 and the left atrial wall 445. The tissue thickness 456 is simply the thickness of fossa ovalis 36 at this location and defines the maximum amount of lateral movement for the pressure sensing capsule 60 prior to entry into the left atrium. Naturally, as force is applied this tissue thickness 456 will be reduced in practice due to compression and deflection.

The above described maximum amount of lateral movement is defined by precluding entry into the left atrium 40. The pressure sensor capsule 60 could be caused to pierce through the fossa ovalis 36 and enter the left atrium 40. In much the same manner as the piercing prong 300 minimally projects into the left atrium 40, advancement of the sensor capsule 60 could be similarly limited. Thus, tissue encapsulation from new tissue growth would be the only attenuating factor for pressure sensing.

Though illustrated as traveling a relatively short span, the threaded track 410 could extend the entire length of lead 16', allowing for complete separation of the sensor capsule 60 from the lead body 16. This could be utilized during implantation; that is, the lead body 16' and housing 70 act as a catheter for the sensor capsule's deployment. Furthermore, it would facilitate replacement of the sensor capsule 60 without necessitating replacement of the housing 70. It should also be appreciated that the threaded track need no extend the entire length of lead 16'. That is, the sensor capsule 60 could be advanced by a stylet (or the sensor actuation member 420 acting as a stylet) up to the threaded track 410. Then, rotation of the capsule 60 will cause the threaded section 400 to engage the threaded track 410. This permits the mechanical advantage provided by the threaded engagement to take place over the distance necessary to contact tissue without requiring that method of travel over the entire length of the lead 16'.

Figure 9:
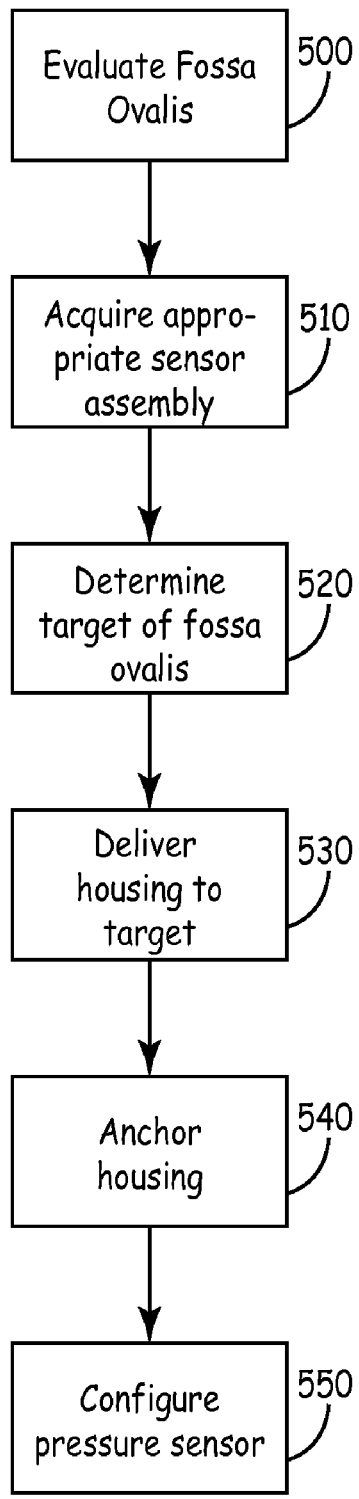
FIG. 9 is a flowchart of a process for providing a pressure sensor in the right atrium to sense pressure within the left atrium.

FIG. 9 is a flowchart describing an overview of selecting and implanting the above described pressure sensing assemblies. Initially, the fossa ovalis of the patient is evaluated (500). This could involve imaging techniques such as fluoroscopy, X-ray, CAT scan, MRI or the like; electrophysiological mapping, intracardiac echocardiography or any other patient specific technique. This is to discern the size and shape of the fossa ovalis so that an appropriate sensor assembly is selected 510. As indicated, this may lead to a sensor assembly that is customized for a given patient. Alternatively, a plurality of models are available and the most appropriate of these models is selected. Finally, a single standard sensor assembly may be provided for all patients and if this is the case or the selected option, the step of evaluating the fossa ovalis 500 becomes optional.

Once the sensor assembly is selected, the "target" is defined (520) with respect to the fossa ovalis. Typically, this means that the center point of the fossa ovalis is identified. The housing assembly is then delivered (530) to this target location. While multiple methods may be used, this typically includes the insertion of a catheter which is guided through the superior vena cava and into the right atrium. The sensor housing is delivered through this catheter and positioned against the fossa ovalis at the targeted location. Using the various techniques discussed above, the properly positioned housing is anchored (540) to the fossa ovalis and/or the fossa limbus. This anchoring may include the generation of a vacuum as well as the advancement of one or more anchoring prongs.

Finally, the pressure sensor itself is configured (550). This may require that the pressure sensor move relative to the housing. Once properly positioned (either via this additional step or via the above anchoring procedure), movement of the fossa ovalis due to left atrial fluid pressure is measured by the pressure sensor and data is provided accordingly. Over time, the effect of the implant, anchoring, and continued presence of a foreign body will cause the cardiac tissue to react by generating tissue or fibrotic growth. This effect will tend to attenuate the output of the pressure signal as change occurs. The process will eventually stabilize and the data provided by the pressure sensor will be relatively consistent.

As disclosed herein, a number of embodiments have been shown and described. These embodiment are not meant to be limiting and many variations are contemplated within the spirit and scope of the invention, as defined by the claim. Furthermore, particular elements illustrated and described with respect to a given embodiment are not limited to that embodiment and may be used in combination with or substituted into other embodiments.

The invention claimed is:

1. An implantable medical device comprising
a pressure sensor disposed within a housing; and,
an anchoring mechanism configured to secure the housing to tissue separating a first chamber from a second chamber such that the pressure sensor is positioned entirely within the first chamber and utilizes a portion of the tissue as a membrane to sense pressure exerted from the second chamber against the tissue.

2. The implantable medical device of claim 1, further comprising:
an implantable cardiac device communicatively coupled with the pressure sensor, wherein data from the pressure sensor is used by the implantable cardiac device to determine an action.

3. The implantable medical device of claim 2, wherein the data is representative of left atrial pressure.

4. The implantable medical device of claim 1, wherein the anchoring mechanism further comprises a deployable anchor member configured to pierce the tissue and secure the housing.

5. The implantable medical device of claim 4, further comprising a lead body having a proximal end and a distal end with the distal end coupled to the housing and a deployment mechanism operable from the proximal end to deploy the anchor member.

6. The implantable medical device of claim 1, further comprising an electrode coupled with the housing to sense electrical signals.

7. The implantable medical device of claim 6, wherein the electrode is deployable from the housing.

8. The implantable medical device of claim 6, wherein the electrode delivers electrical stimulation.

9. The implantable medical device of claim 6, wherein the electrode forms a portion of the anchoring mechanism.

10. The implantable medical device of claim 1 further comprising:
a vacuum channel disposed within the housing and coupled with an opening in the housing proximate the pressure sensor; and
a negative pressure source selectively coupleable with the vacuum channel such that negative pressure within the vacuum channel generates a suction force at the opening.

11. The implantable medical device of claim 10 further comprising a check valve disposed within the vacuum channel and configured to maintain negative pressure between the check valve and the opening when the check valve is in a closed position.

12. A method of implanting a pressure sensor within a right atrial chamber, comprising:
evaluating a fossa ovalis;
selecting an anchorable pressure sensor based upon the evaluation;
delivering the anchorable pressure sensor to the fossa ovalis within a right atrial chamber and;
anchoring the pressure sensor positioned entirely within the right atrial chamber so that contact is made between the pressure sensor and the fossa ovalis so that pressure data provided by the pressure sensor is indicative of pressure within a left atrial chamber.

13. The method of claim 12, wherein anchoring includes deploying a plurality of prongs to pierce tissue and secure the pressure sensor.

14. An implantable medical device comprising:
a pressure sensor disposed within a housing;
at least one anchor prong track located within said housing; and
an anchor prong located within said track and moveable with respect thereto, wherein said anchor prong track is disposed at an acute angle to a horizontal axis of said housing.

15. The implantable medical device of claim 14 further comprising:
an anchor prong deployment mechanism located at least partially within said housing for moving said anchor prong into a tissue-contacting position.

16. The implantable medical device of claim 15 where said prong deployment mechanism is further actuable to retract said anchor prong.

17. The implantable medical device of claim 14 wherein said housing has a tissue-contacting face and wherein said face includes an abrasive ring.

18. The implantable medical device of claim 17 wherein said face further includes a vacuum grid for applying a tissue-attracting vacuum.

19. The implantable medical device of claim 14 wherein said at least one anchor track is positioned to direct said anchor prong into tissue disposed adjacent said housing.

20. The implantable medical device of claim 14 wherein said anchor prong comprises a distal piercing tip and a plurality of tines.

21. The implantable medical device of claim 14 further comprising;
   a vacuum channel disposed within the housing and coupled with an opening in the housing proximate the pressure sensor; and
   a negative pressure source selectively coupleable with the vacuum channel such that negative pressure within the vacuum channel generates a suction force at the opening.

22. The implantable medical device of claim 14 wherein said anchor prong comprises a piercing tip and one or more locking tabs.

23. The implantable medical device of claim 22 further comprising a recoil spring associated with said anchor prong.

24. The implantable medical device of claim 23 wherein said at least one anchor prong track is horizontally disposed.

25. The implantable medical device of claim 14 wherein said pressure sensor comprises a sensor capsule moveable toward and away from tissue adjacent said device.

26. The medical device of claim 25 wherein said sensor capsule is moved by rotation of a threaded member so as to translate rotational movement into lateral movement of said sensor capsule.

* * * * *